(12) United States Patent
Matsubara

(10) Patent No.: US 11,574,384 B2
(45) Date of Patent: Feb. 7, 2023

(54) IMAGE GENERATION DEVICE, IMAGE GENERATION METHOD, AND IMAGE GENERATION PROGRAM TO GENERATE A COMBINATION REGION IMAGE

(71) Applicant: FUJIFILM Corporation, Tokyo (JP)

(72) Inventor: Kenta Matsubara, Ashigarakami-gun (JP)

(73) Assignee: FUJIFILM Corporation, Tokyo (JP)

(*) Notice: Subject to any disclaimer, the term of this patent is extended or adjusted under 35 U.S.C. 154(b) by 155 days.

(21) Appl. No.: 17/116,023

(22) Filed: Dec. 9, 2020

(65) Prior Publication Data

US 2021/0090216 A1   Mar. 25, 2021

Related U.S. Application Data

(63) Continuation of application No. PCT/JP2019/021969, filed on Jun. 3, 2019.

(30) Foreign Application Priority Data

Jul. 13, 2018 (JP) .............................. JP2018-132892

(51) Int. Cl.
   *G06T 3/40* (2006.01)

(52) U.S. Cl.
   CPC ................... *G06T 3/4038* (2013.01)

(58) Field of Classification Search
   CPC .... G06T 3/4038; G02B 21/26; G02B 21/244; G02B 21/367; C12M 1/34;
   (Continued)

(56) References Cited

U.S. PATENT DOCUMENTS 3,786,184 A  *  1/1974  Pieters .................. G02B 27/40
                                                      250/204
2014/0036058 A1   2/2014  Takahashi
                          (Continued)

FOREIGN PATENT DOCUMENTS

JP       2000-357229 A    12/2000
JP       2001-344599 A    12/2001
                (Continued)

OTHER PUBLICATIONS

Partial Supplementary European Seach Report for European Application No. 19833296.7, dated Aug. 2, 2021.
(Continued)

*Primary Examiner* — Siamak Harandi
(74) *Attorney, Agent, or Firm* — Birch, Stewart, Kolasch & Birch, LLP

(57) ABSTRACT

An image generation device includes: a detection unit 43 that performs processing of detecting a specific feature from a plurality of focus images which include an observation target and are in different focus states; a determination unit 44 that determines a parameter indicating a degree of application of a region image to a combination region image in a case where the combination region image is generated from the region image, for each set of the region images in a plurality of corresponding regions respectively corresponding to the plurality of focus images, based on the specific feature detected by the detection unit 43; and a generation unit 45 that generates the combination region image by combining the region images for each of the plurality of corresponding regions based on the parameter determined by the determination unit 44.

16 Claims, 10 Drawing Sheets

(58) Field of Classification Search
CPC ......... H04N 5/23212; H04N 5/232122; H04N 5/232133; H04N 5/23229; C12Q 1/02
See application file for complete search history.

(56) References Cited

U.S. PATENT DOCUMENTS

| | | | |
|---|---|---|---|
| 2015/0153559 A1* | 6/2015 | Sato | H04N 13/395 348/79 |
| 2015/0326798 A1* | 11/2015 | Muto | H04N 5/23229 348/239 |
| 2016/0191784 A1 | 6/2016 | Murayama et al. | |

FOREIGN PATENT DOCUMENTS

| | | |
|---|---|---|
| JP | 2013-236564 A | 11/2013 |
| JP | 2014-29380 A | 2/2014 |
| JP | 2014-71207 A | 4/2014 |
| JP | 2015-108837 A | 6/2015 |

OTHER PUBLICATIONS

International Preliminary Report on Patentability and Written Opinion of the International Searching Authority (Forms PCT/IB/326, PCT/IB/373 and PCT/ISA/237) for International Application No. PCT/JP2019/021969, dated Jan. 28, 2021, with English translation of the Written Opinion.
International Search Report (Form PCT/ISA/210) for International Application No. PCT/JP2019/021969, dated Jul. 30, 2019, with English translation.
Extended European Search Report for corresponding European Application No. 19833296.7, dated Nov. 11, 2021.

* cited by examiner

MOVEMENT DIRECTION
(FORWARD PATH)

MOVEMENT DIRECTION
(BACKWARD ROUTE)

ND IMAGE GENERATION PROGRAM TO GENERATE A COMBINATION REGION IMAGE

IMAGE GENERATION DEVICE, IMAGE GENERATION METHOD, AND IMAGE GENERATION PROGRAM TO GENERATE A COMBINATION REGION IMAGE

CROSS-REFERENCE TO RELATED APPLICATIONS

This application is a Continuation of PCT International Application No. PCT/JP2019/021969 filed on Jun. 3, 2019, which claims priority under 35 U.S.C § 119(a) to Japanese Patent Application No. 2018-132892 filed on Jul. 13, 2018. Each of the above application(s) is hereby expressly incorporated by reference, in its entirety, into the present application.

BACKGROUND OF THE INVENTION

1. Field of the Invention

The disclosed technique relates to an image generation device, an image generation method, and a non-transitory computer readable recording mediums storing an image generation program capable of generating a combination image by combining a plurality of different focus images.

2. Description of the Related Art

A technique of generating an omni-focus image by combining a plurality of single-focus images (focus images) is known. In the technique, an omni-focus combination image is generated by detecting an image of a cell from single-focus images by soft matching, extracting a region image of a region in which a cell is focused from the single-focus images, and combining the region images in focus.

SUMMARY OF THE INVENTION

However, in a case of comparing the region images of corresponding regions in the plurality of single-focus images, in a state where there is only one region image in which a cell is focused, as in the invention described in JP2013-236564A, an omni-focus combination image is obtained by combining only the region images in which a cell is focused. On the other hand, depending on the focus state, a plurality of corresponding region images may include a plurality of region images in which some cells in the image are focused and some cells in the image are not focused.

For example, among the plurality of corresponding region images, in a certain region image, a region in which cells are focused and a region in which cells are not focused may exist in a certain proportion, and in another region image, a region in which cells are focused and a region in which cells are not focused may exist in a proportion different from the above-mentioned proportion. That is, in each image of the plurality of corresponding region images, there is a case where the proportion of the region in which cells are focused and the proportion of the region in which cells are not focused are different, in other words, there is a case where the region images with different focus state are mixed. In such a case, in the invention described in JP2013-236564A, since an omni-focus combination image is generated by combining the region images in which cells are focused, it is difficult to select the region images to be used to generate the omni-focus combination image from the plurality of region images.

The disclosed technique has been made in consideration of the above circumstances, and an object of the disclosed technique is to provide an image generation device, an image generation method, and a non-transitory computer readable recording mediums storing an image generation program capable of generating a combination image even in a case where the region images with different focus states are mixed in the plurality of focus images.

An image generation device according to a disclosed technique includes: a detection unit that performs processing of detecting a specific feature from a plurality of focus images which include an observation target and are in different focus states; a determination unit that determines a parameter indicating a degree of application of a region image to a combination region image in a case where the combination region image is generated from the region image, for each set of the region images in a plurality of corresponding regions respectively corresponding to the plurality of focus images, based on the specific feature detected by the detection unit; and a generation unit that generates the combination region image by combining the region images for each of the plurality of corresponding regions based on the parameter determined by the determination unit.

Here, in a case where the plurality of images are two images, the degree of application is set as, for example, a ratio of 100:0, 70:30, 50:50, or the like.

In the image generation device, the determination unit may determine a parameter for a set of the region images that do not include the detected specific feature in any region image, based on a parameter determined for a set of the region images that include the detected specific feature in any region image.

In the image generation device, the determination unit may determine the parameter for the set of the region images that do not include the specific feature in any region image, based on a distance from the corresponding regions of the set of the region images that include the specific feature in any region image to the corresponding regions of the set of the region images that do not include the specific feature in any region image.

In the image generation device, the determination unit may determine the parameter based on a predetermined degree of application for a set of the region images that do not include the specific feature in any region image.

In the image generation device, the generation unit may generate a combination image by arranging and combining the combination region images according to positions of the corresponding regions.

In the image generation device, the specific feature may be at least one of a feature of an image of a target object included in the observation target or a feature of an image of a non-target object included in the observation target.

In the image generation device, in a case where the feature of the image of the target object is included in the region image, the determination unit may determine the parameter by setting a degree of application of the region image including the feature of the image of the target object to the combination region image to be higher than a degree of application of the region image that does not include the feature of the image of the target object to the combination region image, and in a case where the feature of the image of the non-target object is included in the region image, the determination unit may determine the parameter by setting a degree of application of the region image including the feature of the image of the non-target object to the combination region image to be lower than a degree of application of the region image that does not include the feature of the image of the non-target object to the combination region image.

In the image generation device, in a case where a plurality of region images including the feature of the target object exist in a set of the region images in one corresponding region, the determination unit may determine a parameter for each region image based on a proportion of an area occupied by the feature of the target object in each region image.

In the image generation device, the target object may be a living cell, and the non-target object may be a foreign matter other than the living cell that is included in the observation target. Examples of the foreign matter include dead cells and detritus.

In the image generation device, the determination unit may determine the parameter by setting a degree of application of the region image including a feature of an image of the living cell to the combination region image to be higher than a degree of application of the region image that does not include the feature of the image of the living cell to the combination region image.

In the image generation device, the determination unit may determine the parameter by setting a degree of application of the region image including a feature of an image of the foreign matter to the combination region image to be lower than a degree of application of the region image that does not include the feature of the image of the foreign matter to the combination region image.

In the image generation device, the target object may include, in addition to the living cell, a pattern represented on a bottom surface of an accommodation portion, and the determination unit may determine the parameter by setting a degree of application of the region image including a feature of an image of the pattern to the combination region image to be higher than a degree of application of the region image that does not include both of the feature of the image of the living cell and the feature of the image of the foreign matter to the combination region image.

The image generation device may further include a warning unit that outputs a warning for the corresponding region in which the specific feature is not detected in any region image.

An image generation method according to another disclosed technique includes: a detection step of performing processing of detecting a specific feature from a plurality of focus images which include an observation target and are in different focus states; a determination step of determining a parameter indicating a degree of application of a region image to a combination region image in a case where the combination region image is generated from the region image, for each set of the region images in a plurality of corresponding regions respectively corresponding to the plurality of focus images, based on the specific feature detected by the detection step; and a generation step of generating the combination region image by combining the region images for each of the plurality of corresponding regions based on the parameter determined by the determination step.

A non-transitory computer readable recording mediums storing an image generation program according to still another disclosed technique causes a computer to execute: a detection step of performing processing of detecting a specific feature from a plurality of focus images which include an observation target and are in different focus states; a determination step of determining a parameter indicating a degree of application of a region image to a combination region image in a case where the combination region image is generated from the region image, for each set of the region images in a plurality of corresponding regions respectively corresponding to the plurality of focus images, based on the specific feature detected by the detection step; and a generation step of generating the combination region image by combining the region images for each of the plurality of corresponding regions based on the parameter determined by the determination step.

Further, an image generation device according to still another aspect of the present disclosure includes a processor configured to: detect a specific feature from a plurality of focus images which include an observation target and are in different focus states; determine a parameter indicating a degree of application of a region image to a combination region image in a case where the combination region image is generated from the region image, for each set of the region images in a plurality of corresponding regions respectively corresponding to the plurality of focus images, based on the detected specific feature; and generate the combination region image by combining the region images for each of the plurality of corresponding regions based on the determined parameter.

According to the disclosed technique, a parameter indicating a degree of application of a region image to a combination region image is determined for each corresponding region, and the region images are combined based on the parameter. Thereby, according to the disclosed technique, even in a case where a region image in which a cell is focused over the entire image cannot be obtained from a plurality of region images, a combination image can be generated.

DESCRIPTION OF THE PREFERRED EMBODIMENTS

Figure 1:
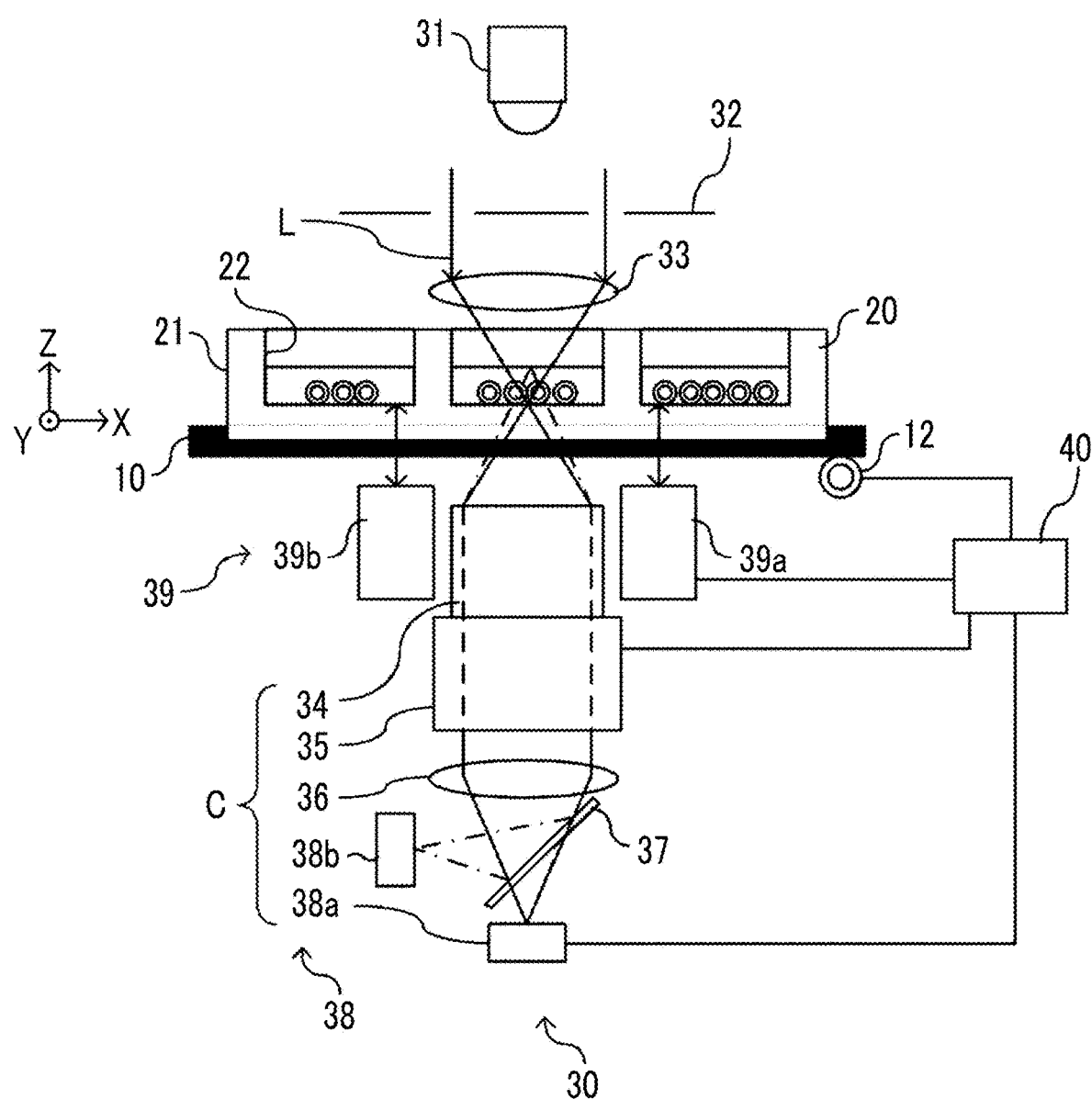
FIG. 1 is a diagram illustrating a schematic configuration of an observation device according to an embodiment of a disclosed technique.

Hereinafter, an example of an embodiment of a disclosed technique will be described with reference to the drawings. In the drawings, the same or equivalent components and portions are denoted by the same reference numerals. Further, dimensional ratios in the drawings are exaggerated for convenience of explanation, and may be different from actual ratios.

Figure 2:
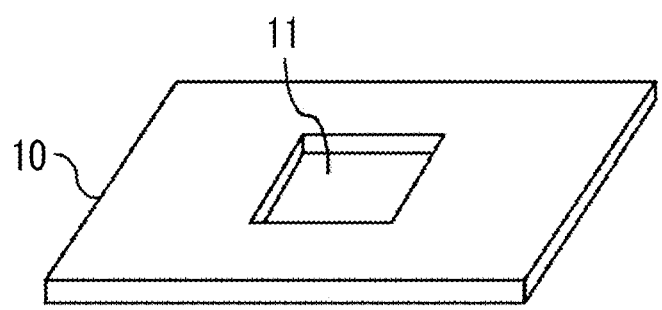
FIG. 2 is a diagram illustrating an example of a placing stand.
Figure 3:
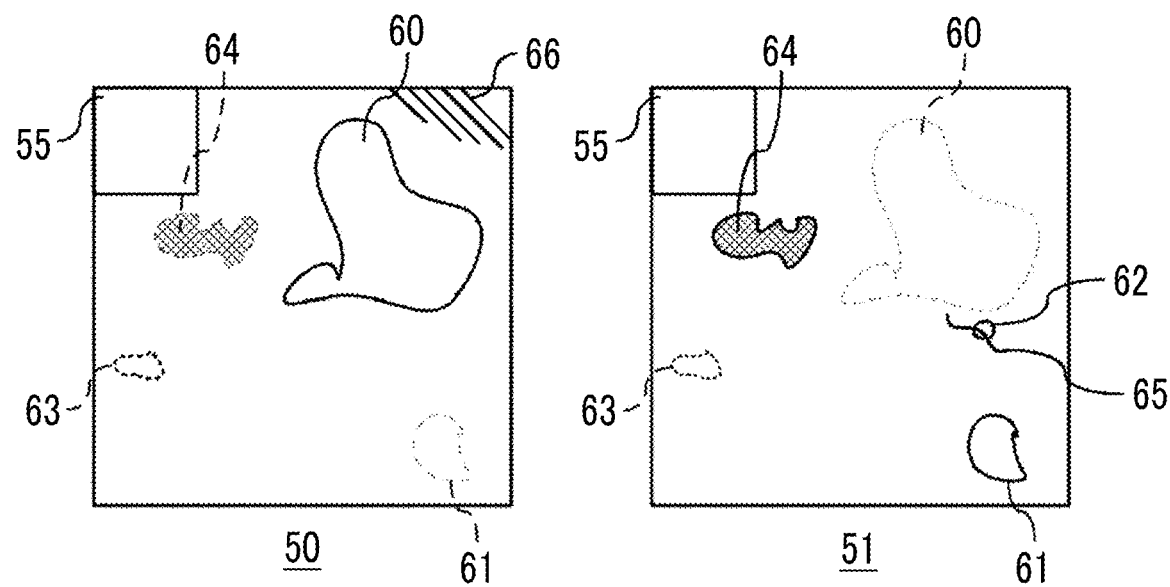
FIG. 3 is a diagram illustrating an example of a phase difference image which is imaged by an imaging unit.

FIG. 1 is a diagram illustrating a schematic configuration of an observation device according to an embodiment of a disclosed technique. FIG. 2 is a diagram illustrating an example of a placing stand. FIG. 3 is a diagram illustrating an example of a phase difference image which is imaged by an imaging unit.

The observation device is a device for observing, as an observation target, a culture container 20 placed on a placing stand 10 and a culture solution accommodated in the culture container 20 by a microscope device 30. The placing stand 10 and the microscope device 30 are controlled by a control unit 40. Each component will be described in order.

The placing stand 10 is a stage on which the culture container 20 can be placed. As illustrated in FIG. 2, a rectangular opening 11 is formed in a center portion of the placing stand 10. The culture container 20 is placed on a member forming the opening 11, and is configured to allow light for observation by the microscope device 30 to pass.

A moving unit 12 is attached to the placing stand 10. The moving unit 12 can freely move the placing stand 10 in an X direction and a Y direction which are perpendicular to each other. The X direction and the Y direction are directions perpendicular to a Z direction, and are directions perpendicular to each other in a horizontal plane. In the present embodiment, it is assumed that the X direction is a main scanning direction and the Y direction is a sub scanning direction. The moving unit 12 is configured with an actuator including a piezoelectric element and the like. The movement of the placing stand 10 in an X-Y plane is controlled by the control unit 40. The placing stand 10 moves on the X-Y plane, and thus the culture container 20 on the placing stand 10 moves with respect to the microscope device 30.

In the present embodiment, an example in which the microscope device 30 changes an observation position of the observation target by moving the placing stand 10 with respect to the microscope device 30 is described. On the other hand, the present disclosure is not limited thereto. The microscope device 30 may be moved with respect to the placing stand 10, or both of the placing stand 10 and the microscope device 30 may be moved with respect to each other. Any form may be adopted as long as at least one of the culture container 20 placed on the placing stand 10 or the microscope device 30 relatively moves with respect to the other. In the present disclosure, for example, even in a case where a position of the microscope device 30 is fixed and only the culture container 20 is moved, it is expressed that "the microscope device 30 relatively moves with respect to the culture container 20". Further, in the present disclosure, even in a case where any one of the microscope device 30 or the culture container 20 actually moves, a trajectory according to the relative movement is expressed as a "scanning trajectory".

Further, instead of moving the culture container 20 placed on the placing stand 10, by providing a grip portion for gripping at least one portion of the culture container 20 and moving the grip portion, the culture container 20 may be moved in the X-Y plane.

In the culture container 20, a plurality of accommodation portions 22 are formed on a flat-shaped plate 21. As the culture container 20, for example, a petri dish, a dish, a well plate, or the like may be used. The accommodation portion 22 is, for example, a circular-shaped recess portion when seen in a plan view, and is also called a well. The accommodation portion 22 accommodates target objects such as various cells soaked in the culture solution as the observation target. The target objects are mainly living cells. The cells to be accommodated in the accommodation portion 22 include pluripotent stem cells such as iPS cells and ES cells, nerves differentiated and induced from stem cells, cells of a skin, a myocardium, and a liver, and cells of a skin, a retina, a myocardium, a corpuscle, a nerve, and an organ which are taken from a human body. The culture solution may also contain unintended detritus or dead cells. A bottom surface of the accommodation portion 22 is processed. As an example of the processing of the bottom surface of the accommodation portion 22, a regular fine pattern is formed. The pattern includes regular repetition of a plurality of straight lines or curved lines, a plurality of concentric rings, repetition of regular irregularities, and the like. The pattern is formed on the bottom surface of the accommodation portion 22 by patterning, for example, by blasting. Since the bottom surface of the accommodation portion 22 is processed, cells are likely to be fixed on the bottom surface.

The microscope device 30 images a phase difference image of an observation target. In order to obtain a high-magnification image, the microscope device 30 images partial images of the observation target and the culture container 20 with a field of view narrower than each accommodation portion 22 of the culture container 20. As described above, the culture container 20 moves with respect to the microscope device 30, and the microscope device 30 scans the culture container 20. Thus, a series of partial images are obtained.

The microscope device 30 includes a light source 31, a slit 32, a condenser lens 33, an objective lens 34, a focus adjustment mechanism 35, an image-forming lens 36, a half mirror 37, an imaging unit 38, and a measurement unit 39.

The light source 31 emits white light. As the slit 32, a ring-shaped slit that passes the white light emitted from the light source 31 is formed on a light-shielding plate that shields the white light. The white light passes through the slit, and thus ring-shaped illumination light L is formed. The condenser lens 33 focuses the ring-shaped illumination light L on the observation target.

The objective lens 34 is disposed to face the condenser lens 33 via the culture container 20. The objective lens 34 forms an image of the observation target in the culture container 20. The focus adjustment mechanism 35 includes a phase difference lens that can move in an optical axis direction (Z direction), and performs autofocus control by moving the phase difference lens in the optical axis direction. By the autofocus control, contrast of the phase difference image, which is imaged by the imaging unit 38 via the half mirror 37, is adjusted. In order to extend a depth of field, the imaging unit 38 acquires a plurality of focus images with different focus states at the same position on the X-Y plane in the accommodation portion 22 and at a plurality of different positions in the Z direction, and the focus adjustment mechanism 35 performs autofocus control at imaging positions at which the imaging unit 38 acquires the focus images. In the present embodiment, at the same position on the X-Y plane, the autofocus control is performed twice so as to obtain focus images at the same position on the X-Y plane and at two positions in the Z direction (a position on a bottom surface of the accommodation portion 22 and a position between the bottom surface and a liquid surface of the culture solution). Details of the imaging unit 38 will be described later.

The movement of the phase difference lens in the optical axis direction can be realized by driving an actuator such as a piezoelectric element based on a signal from the control unit 40. On the other hand, a configuration for driving the phase difference lens is not limited to the piezoelectric element. A configuration capable of moving the phase difference lens in the Z direction may be used, or other known configurations may be used. Further, a configuration capable of changing a magnification of the phase difference lens may be used. Specifically, a configuration capable of replacing the phase difference lens or the focus adjustment mechanism 35 with a component having a different magnification may be used. The replacement may be automatically performed, or may be manually performed by a user.

The phase difference image which passes through the focus adjustment mechanism 35 is entered to the image-forming lens 36, and the image-forming lens 36 forms the phase difference image on the imaging unit 38.

The imaging unit 38 is fixedly attached to the measurement unit 39, and images the phase difference image, which is formed by the image-forming lens 36 and is passed through the half mirror 37 or reflected by the half mirror 37. In the present embodiment, the imaging unit 38 includes two imaging units of an imaging unit 38a and an imaging unit 38b. The imaging unit 38a and the imaging unit 38b are disposed apart from the image-forming lens 36 by a distance required to image the phase difference image at the same position on the X-Y plane and at different positions in the Z direction. The imaging units 38a and 38b are imaging elements such as a charge-coupled device (CCD) image sensor or a complementary metal-oxide semiconductor (CMOS) image sensor. As the imaging element, an imaging element in which red, green, and blue (RGB) color filters are provided may be used, or a monochrome imaging element may be used. Hereinafter, the phase difference image is also simply referred to as an image. In the present embodiment, a case where the imaging unit 38 includes two imaging units of the imaging unit 38a and the imaging unit 38b will be described. On the other hand, the imaging unit 38 is not limited thereto, and may include three or more imaging units.

The imaging unit 38a and the imaging unit 38b image images of the culture container 20 at the same position on the X-Y plane and at different imaging positions in the Z direction. For example, the imaging unit 38a and the imaging unit 38b image partial images 50 and 51 as illustrated in FIG. 3. The partial images 50 and 51 include images of living cells 60 to 63, images of dead cells 64, images of detritus 65, images of patterns 66 on the bottom surface of the accommodation portion, and the like. In the example illustrated in FIG. 3, in the partial image 50, the living cell 60 is focused, while the living cells 61 and 63 and the dead cell 64 are not focused. In the partial image 51, the living cells 61 and 62, the dead cell 64, and the detritus 65 are focused, while the living cells 60 and 63 are not focused. As described above, in the partial images 50 and 51 which are imaged at the same position on the X-Y plane and at different imaging positions in the Z direction, the images of the living cells 60 to 63 and the pattern 66, which are target objects, and the images of the dead cells 64 and the detritus 65, which are non-target objects, have different appearances.

In the following, the objective lens 34, the focus adjustment mechanism 35, the image-forming lens 36, and the imaging unit 38 are collectively referred to as an image-forming optical system C.

The measurement unit 39 continuously detects a position of the culture container 20 placed on the placing stand 10 in the Z direction, along a scanning trajectory according to relative movement of at least one of the culture container 20 or the imaging unit 38.

Specifically, the measurement unit 39 includes a first displacement sensor 39a and a second displacement sensor 39b. The first displacement sensor 39a and the second displacement sensor 39b are provided side by side in the X direction illustrated in FIG. 1 with the image-forming optical system C interposed therebetween. The first displacement sensor 39a and the second displacement sensor 39b in the present embodiment are laser displacement meters, which detect a position of the bottom surface of the accommodation portion 22 of the culture container 20 in the Z direction by irradiating the culture container 20 with laser light and detecting reflected light of the laser light and measure a distance from the imaging unit 38 to the bottom surface of the accommodation portion 22. The bottom surface of the accommodation portion 22 is a boundary surface between the bottom surface of the accommodation portion 22 and the culture solution accommodated in the accommodation portion 22, that is, an observation target placement surface.

The distance from the imaging unit 38 to the bottom surface of the accommodation portion 22 detected by the measurement unit 39 is output to the control unit 40. The control unit 40 performs autofocus control (focus control) by controlling the focus adjustment mechanism 35 based on the distance which is input. The detection of the position of the culture container 20 by the first displacement sensor 39a and the second displacement sensor 39b and the autofocus control will be described in detail later.

Figure 4:
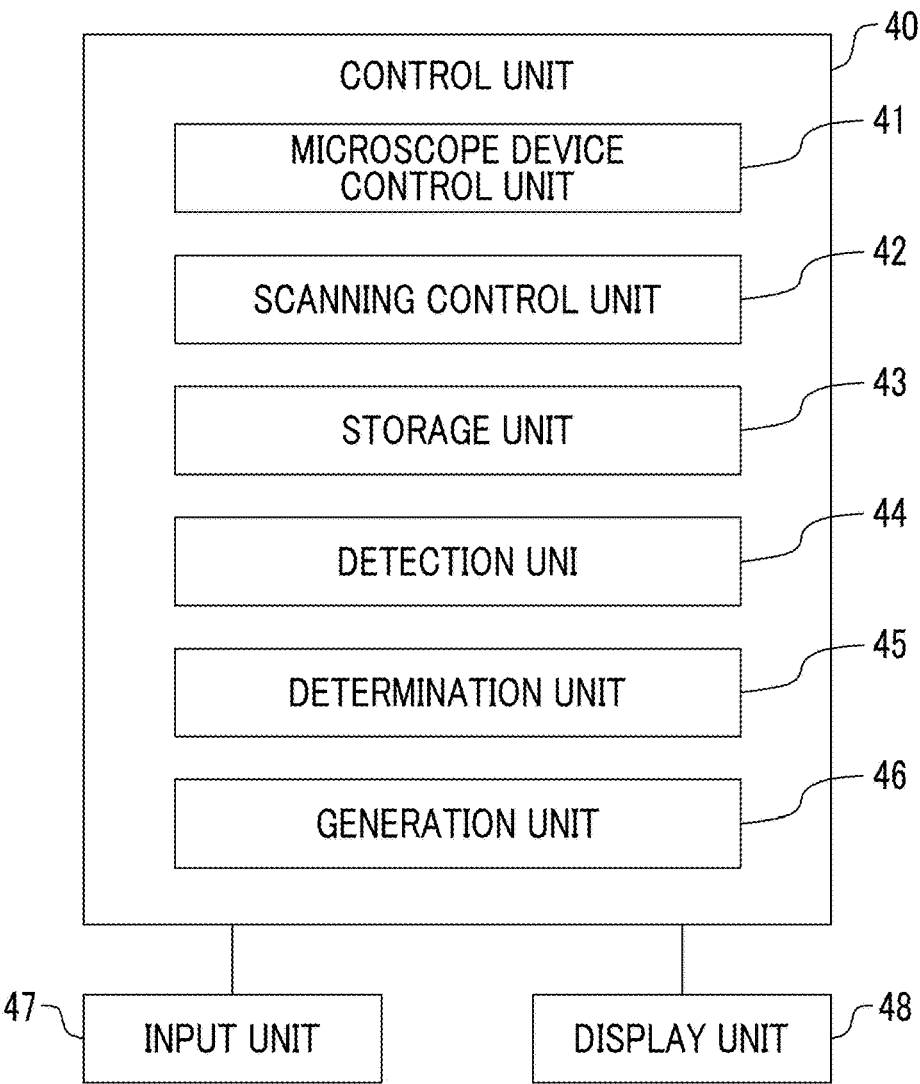
FIG. 4 is a block diagram illustrating a configuration of a control unit according to the embodiment of the disclosed technique.

Next, a configuration of the control unit 40 that controls the microscope device 30 will be described. FIG. 4 is a block diagram illustrating a configuration of the control unit according to the embodiment of the disclosed technique.

The control unit 40 controls the entire microscope device 30 as described above, and performs various processing. The control unit 40 includes a microscope device control unit 41, a scanning control unit 42, a storage unit 43, a detection unit 44, a determination unit 45, a generation unit 46, an input unit 47, and a display unit 48. The control unit 40 is configured with a computer including a central processing unit (CPU), a semiconductor memory, a storage, and the like. An embodiment of an observation program according to the present disclosure is installed in a storage. The observation program is executed by the CPU, and thus the observation program functions as the microscope device control unit 41, the scanning control unit 42, the detection unit 44, the determination unit 45, and the generation unit 46 illustrated in FIG. 4.

The microscope device control unit 41 controls the focus adjustment mechanism 35 based on the position information of the culture container 20 in the Z direction that is detected by the measurement unit 39 as described above. The phase difference lens is moved in the optical axis direction by driving of the focus adjustment mechanism 35, and thus autofocus control is performed. In order to extend a depth of field, autofocus control is performed multiple times in the Z direction at the same position on the X-Y plane such that a plurality of focus images with different focus states can be obtained at the same position on the X-Y plane. In the present embodiment, the microscope device control unit 41 controls the focus adjustment mechanism 35 such that two focus images with different focus states are imaged at each imaging position on the X-Y plane. Instead of moving the image-forming lens 36 by the focus adjustment mechanism 35 (imaging at different imaging positions in the Z direction), a plurality of focus images may be imaged by changing a focusing method at one imaging position in the Z direction. In this specification, the "focus image" is an image in which at least a part of the image is focused.

Further, the microscope device control unit 41 controls the imaging by the imaging unit 38a and the imaging unit 38b in a case where the culture container 20 is scanned. Basically, an imaging timing during scanning is stored in advance in the storage unit 43, and the microscope device control unit 41 performs imaging based on the stored timing.

The scanning control unit 42 moves the placing stand 10 in the X direction and the Y direction by driving and controlling the moving unit 12. The storage unit 43 stores various data such as imaging timings by the imaging unit 38a and the imaging unit 38b and an observation program for realizing each functional unit.

The detection unit 44 performs processing of detecting a specific feature from the plurality of focus images, which are obtained by imaging the culture solution accommodated in the accommodation portion 22 by the imaging units 38a and 38b at a plurality of different imaging positions in the Z direction. The specific feature is at least one of a feature of an image of a target object included in the culture solution as the observation target or a feature of an image of a non-target object included in the culture solution. The target object is a living cell, and the non-target object is a foreign matter included in the culture solution other than the living cell. Examples of the foreign matter include dead cells and detritus. In addition, the target object may include a pattern formed on the bottom surface of the accommodation portion 22. In a case where the target object includes a pattern, the detection unit 44 detects a pattern from the plurality of focus images. As described above, living cells are likely to be attached to the pattern on the bottom surface of the accommodation portion 22. Thus, in a case where the pattern is detected, living cells may be indirectly detected. For this reason, depending on a focus state (a degree of focusing), in some cases, the plurality of focus images, which are imaged at different imaging positions in the Z direction, may not include focus images in which living cells are focused, and as a result, living cells may not be directly detected by soft matching by a computer. Even in such a case, in a case where the pattern of the bottom surface of the accommodation portion is detected, by using a region image in which the pattern is detected to a combination image, a user may be able to determine a living cell by visual confirmation. Therefore, a region image in which the bottom surface of the accommodation portion is focused is useful.

In a case where a combination region image is generated from the partial images 50 and 51 at different imaging positions in the Z direction, the determination unit 45 determines a parameter indicating a degree (weight) of application in a case where a region image of each image is applied to a combination region image, based on the specific feature detected by the detection unit 44. The determination unit 45 determines a parameter for each set of region images in a plurality of corresponding regions corresponding to the partial images 50 and 51 at different imaging positions in the Z direction. The corresponding regions are regions corresponding to the same position among a plurality of partial images. For example, in a case where the partial images 50 and 51 illustrated in FIG. 3 are divided into grid shapes, grids at the same position are the corresponding regions 55. In FIG. 3, only the corresponding regions 55 at the upper left are illustrated. On the other hand, not only the grids at the upper left, but also all the grids at the same position between the partial images 50 and 51 are the corresponding regions 55. The region images are images that are represented in the corresponding regions 55 of the partial images 50 and 51, and each set of the region images corresponds to the corresponding regions 55 at the same position. The parameter is a degree of application in a case where the region images included in a set are applied to a combination region image, and is set as a ratio such as 100:0, 70:30, 50:50, or the like. In the present embodiment, for easy understanding of the ratio, a value of the ratio is determined as a percentage such that the total value becomes 100. In a case of 100:0, the ratio means that one region image included in a set is used to the combination region image at 100% and the other region image is not used at all to the combination region image. In a case of 70:30, the ratio means that one region image included in a set is used to a combination region image at 70% and the other region image is used to the combination region image at 30%. Details of a method of determining the parameter will be described later. The combination region image is an image formed by combining a plurality of region images, which are included in the corresponding regions, according to a superimposition parameter. In the present embodiment, an example in which the two partial images 50 and 51 are combined is described. On the other hand, it goes without saying that the image generation device according to the present embodiment can be applied to a case where three or more images are combined.

The generation unit 46 generates a combination region image by combining the region images of the plurality of partial images for each of the plurality of corresponding regions based on the parameter determined by the determination unit 45. For example, it is assumed that an application degree of 70:30 is set as a parameter for a set of the region images representing certain corresponding regions. In this case, the generation unit 46 sets a pixel value of the combination region image by, for example, multiplying a brightness value of a pixel of one region image by 0.7, multiplying a brightness value of a pixel of the other region image by 0.3, and summing up the brightness values for each corresponding pixel. Thereby, a combination region image in which the brightness is increased in proportion to the parameter is generated. The generation unit 46 generates a desired combination image (partial image) by further combining the combination region images, which are obtained by combining the region images of all the corresponding regions, side by side at positions of the corresponding regions. The generation unit 46 generates combination images by performing the same processing on all of a series of the partial images imaged by the microscope device 30, and generates one entire combination image by combining a series of the combination images.

The input unit 47 includes a mouse and a keyboard, and receives various required data and various setting input by the user. The input unit 47 according to the present embodiment receives, for example, input of shape information of the culture container 20 and input of data on the imaging position.

The display unit 48 includes, for example, a liquid crystal display, and displays the entire combination image generated by the generation unit 46 as described above. Alternatively, the display unit 48 may be configured with a touch panel such that the display unit 48 also serves as the input unit 47.

Next, a movement control of the placing stand 10 by the scanning control unit 42 and a control of the microscope device 30 by the microscope device control unit 41 will be described in detail.

Figure 5:
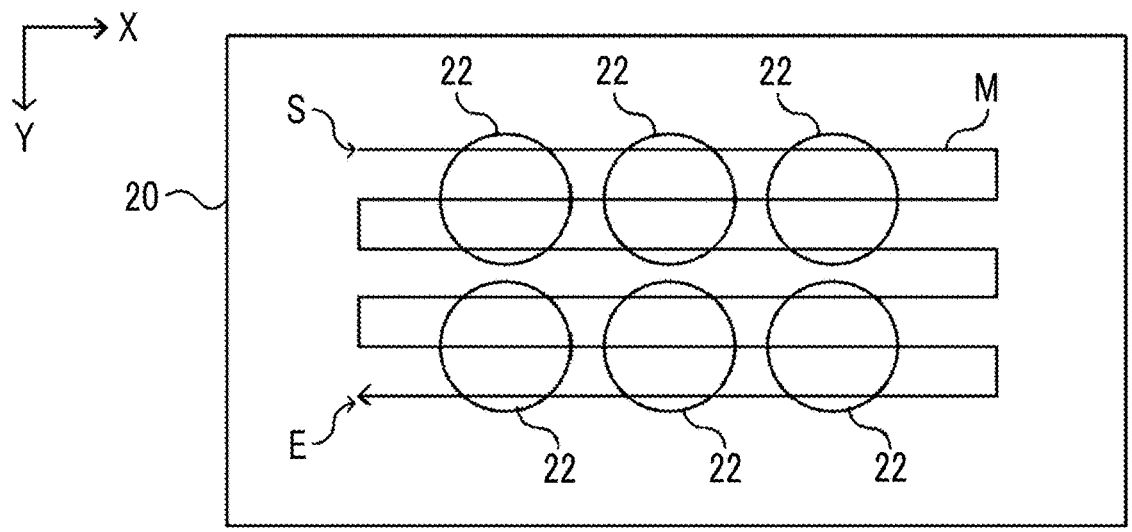
FIG. 5 is a diagram illustrating a scanning path in a culture container by a solid line.
Figure 6:
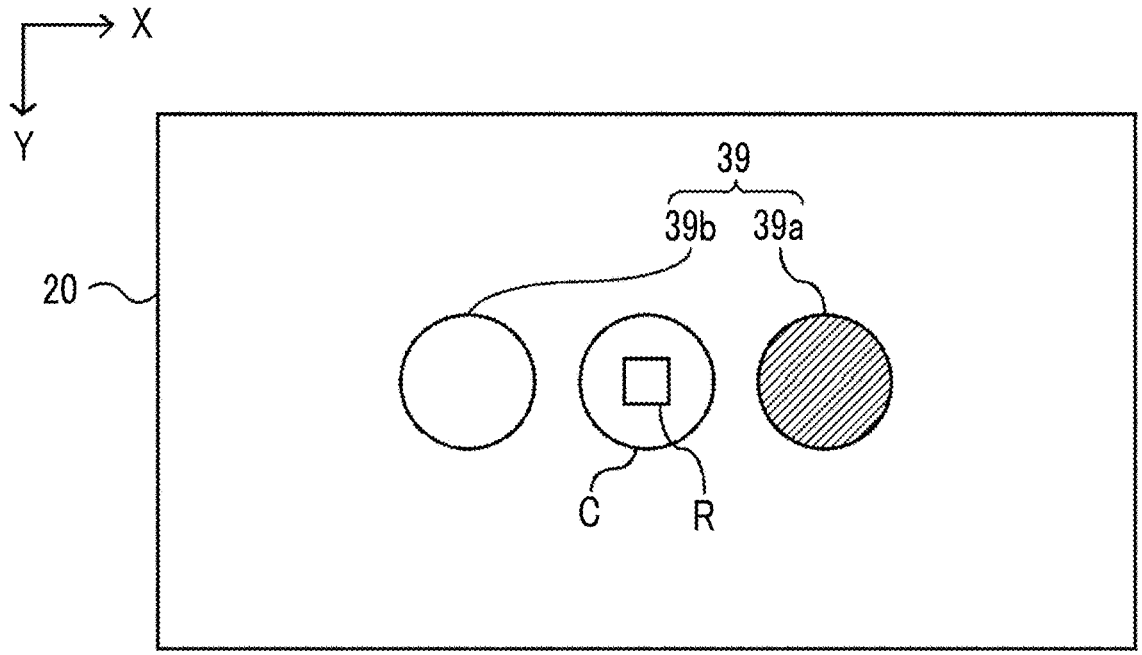
FIG. 6 is a diagram illustrating a positional relationship between a culture container and a first displacement sensor and a second displacement sensor in a case where a field of view is located at a certain position in the culture container.
Figure 7:
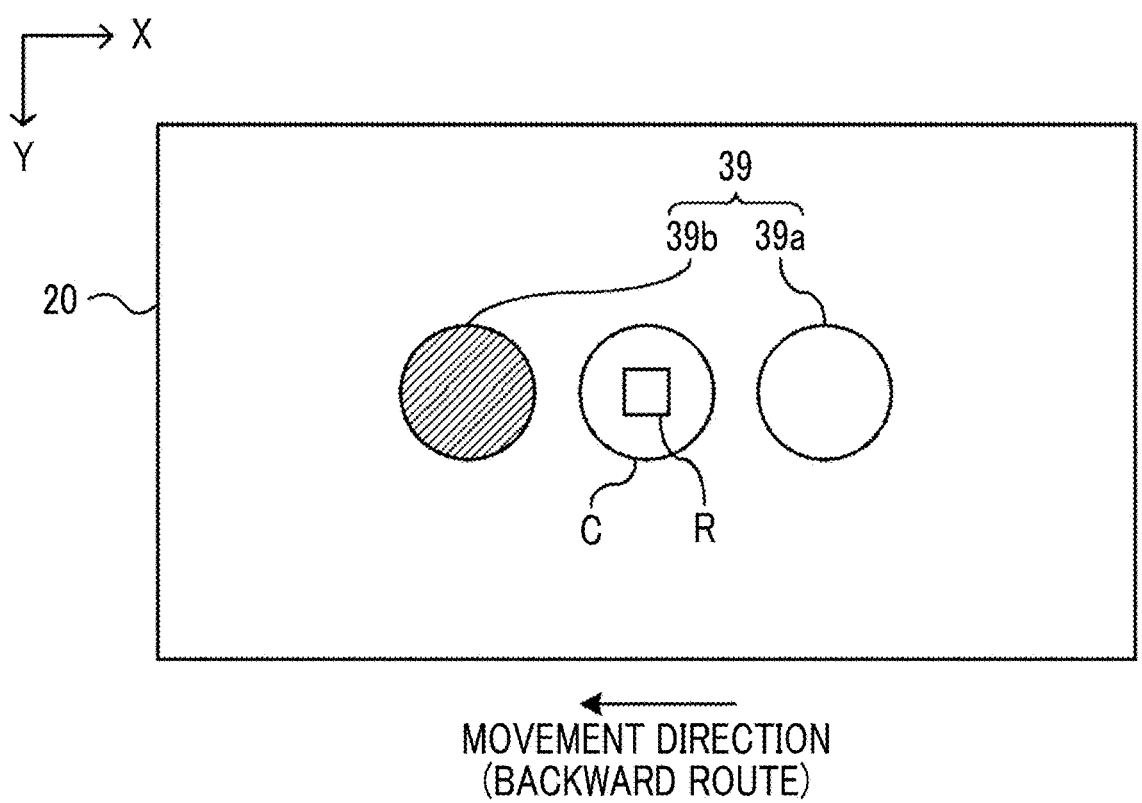
FIG. 7 is a diagram illustrating a positional relationship between a culture container and a first displacement sensor and a second displacement sensor in a case where a field of view is located at a certain position in the culture container.

FIG. 5 is a diagram illustrating a scanning path in the culture container by a solid line M. FIG. 6 and FIG. 7 are diagrams illustrating a positional relationship between the culture container and the first displacement sensor and the second displacement sensor in a case where a field of view is located at a certain position in the culture container.

In the present embodiment, the placing stand 10 is moved in the X direction and the Y direction by a control by the scanning control unit 42, and thus the microscope device 30 two-dimensionally scans the inside of the culture container 20. In scanning processing, in each field of view of the microscope device 30, a partial image of the observation target is imaged. In the present embodiment, a well plate including six accommodation portions 22 is used as the culture container 20.

As illustrated in FIG. 5, the field of view of the microscope device 30 moves from a scanning start point S to a scanning end point E along a solid line M. That is, after scanning is performed in the positive X direction (right direction in FIG. 5), the field of view is moved in the Y direction (down direction in FIG. 5), and then scanning is performed in the opposite negative X direction (left direction in FIG. 5). Next, the field of view is moved again in the Y direction, and then scanning is performed again in the positive X direction. In this way, reciprocation movement of the field of view in the X direction and movement of the field of view in the Y direction are repeatedly performed, and thus the inside of the culture container 20 is two-dimensionally scanned.

In the present embodiment, as illustrated in FIG. 6 and FIG. 7, the first displacement sensor 39a and the second displacement sensor 39b are provided side by side in the X direction with the image-forming optical system C interposed therebetween. In the field of view R of the image-forming optical system C, the inside of the culture container 20 is two-dimensionally scanned as described above. At this time, a position of the culture container 20 in the Z direction is detected at a position on a front side in the movement direction of the field of view R than a position of the field of view R of the image-forming optical system C with respect to the culture container 20. Specifically, in a case where the field of view R is moved in a direction of an arrow illustrated in FIG. 6 (right direction in FIG. 6), a position of the culture container 20 in the Z direction is detected by the first displacement sensor 39a, which is on the front side in the movement direction of the field of view R, among the first displacement sensor 39a and the second displacement sensor 39b. In a case where the field of view R is moved from a position illustrated in FIG. 6 to a position of the first displacement sensor 39a, autofocus control is performed using position information of the culture container 20 in the Z direction, which is detected in advance, and the partial images (the plurality of images) are imaged.

On the other hand, in a case where the field of view R is moved in a direction of an arrow illustrated in FIG. 7 (left direction in FIG. 7), a position of the culture container 20 in the Z direction is detected by the second displacement sensor 39b, which is on the front side in the movement direction of the field of view R, among the first displacement sensor 39a and the second displacement sensor 39b. In a case where the field of view R is moved from a position illustrated in FIG. 7 to a position of the second displacement sensor 39b, autofocus control is performed using position information of the culture container 20 in the Z direction, which is detected in advance, and the partial images are imaged.

In this way, the detection of the culture container 20 using the first displacement sensor 39a and the detection of the culture container 20 using the second displacement sensor 39b are switched according to the movement direction of the field of view R. Thereby, prior to imaging of the partial images in the field of view R, the position information of the culture container 20 in the Z direction at the position of the field of view R can be always acquired.

The microscope device control unit 41 performs autofocus control by controlling driving of the focus adjustment mechanism 35 based on the position information of the culture container 20 in the Z direction that is detected in advance as described above. Specifically, a relationship between the position information of the culture container 20 in the Z direction and a movement amount of the image-forming optical system C in the optical axis direction is set in advance in the microscope device control unit 41. Here, two movement amounts of the image-forming optical system C in the optical axis direction are associated with one position of the culture container 20 in the Z direction. Thereby, it is possible to perform imaging by the imaging unit 38a and the imaging unit 38b at two different imaging positions in the Z direction. The microscope device control unit 41 obtains a movement amount of the image-forming optical system C in the optical axis direction based on the input position information of the culture container 20 in the Z direction, and outputs a control signal according to the movement amount to the focus adjustment mechanism 35. The focus adjustment mechanism 35 is driven based on the input control signal. Thereby, the phase difference lens moves in the optical axis direction, and thus focus adjustment is performed according to the position of the culture container 20 in the Z direction.

Next, generation of the combination image by the generation unit 46 will be described in detail.

Figure 8:
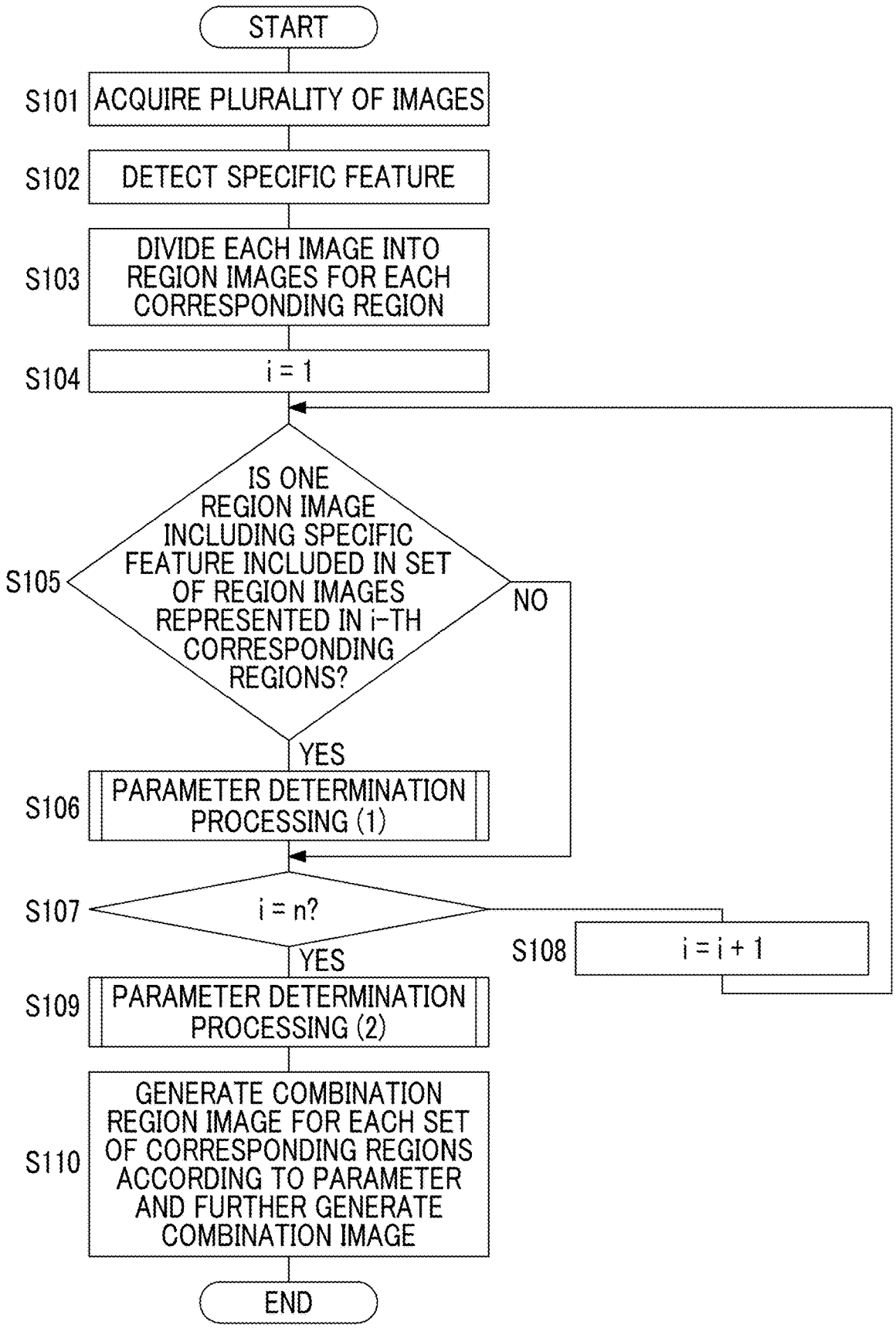
FIG. 8 is a flowchart illustrating a flow of generation of a combination region image.
Figure 9:
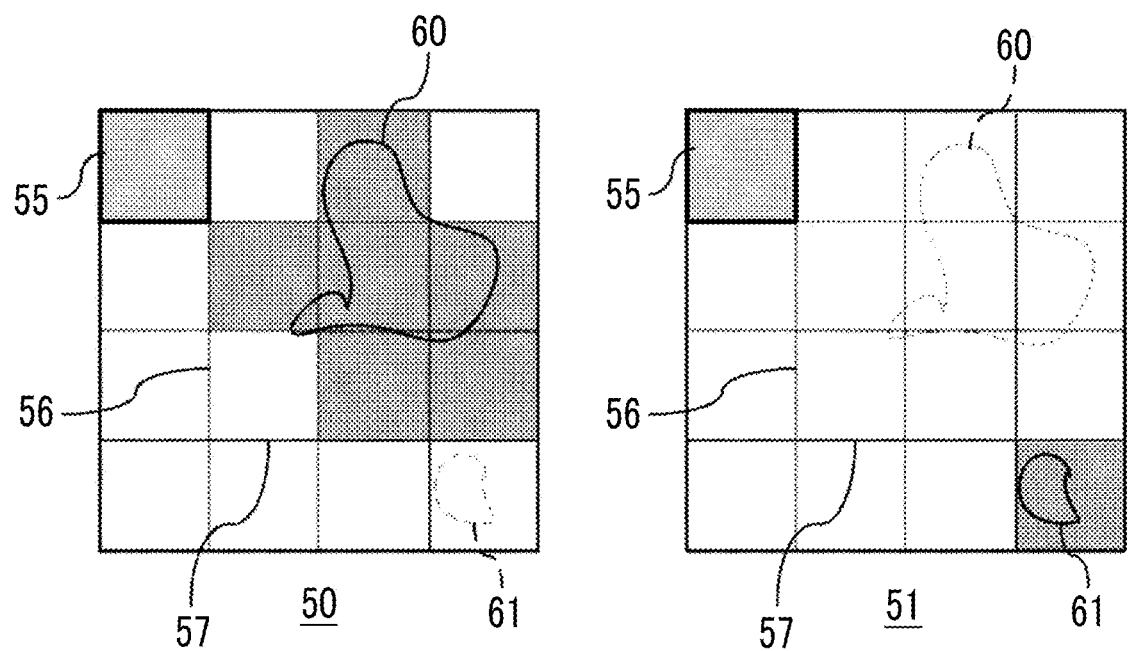
FIG. 9 is a diagram illustrating a method of detecting a specific feature.

FIG. 8 is a flowchart illustrating a flow of generation of the combination image. FIG. 9 is a diagram illustrating a method of detecting a specific feature. In FIG. 9, a plurality of vertical lines 56 and a plurality of horizontal lines 57 in the partial images 50 and 51 are not lines drawn as images, but lines for dividing the partial images 50 and 51 into a plurality of corresponding regions having a grid shape.

The control unit 40 (CPU) reads a combination program from a storage and loads the combination program into a RAM, and thus processing illustrated in FIG. 8 is realized.

The control unit 40 acquires a plurality of images at different imaging positions in the Z direction from the imaging unit 38a and the imaging unit 38b (step S101).

The detection unit 44 of the control unit 40 detects a specific feature from the plurality of images (step S102). The specific feature includes both of a feature of an image of a target object and a feature of an image of a non-target object, as described above. In the description of the flowchart, living cells and a pattern on the bottom surface of the accommodation portion 22 are detected as target objects, and dead cells and foreign matters such as detritus are detected as non-target objects. The control unit 40 detects living cells, the pattern on the bottom surface of the accommodation portion 22, and foreign matters such as dead cells and detritus by image processing such as pattern matching.

For the pattern matching, pieces of feature data of living cells, the pattern on the bottom surface, dead cells, and detritus are stored in advance in the storage of the control unit 40. For example, as illustrated in FIG. 9, the control unit 40 detects living cells (group) 60 in the partial image 50, and detects living cells (group) 61 in the partial image 51.

The control unit 40 divides each image into region images for each corresponding region (step S103). Specifically, as illustrated in FIG. 9, the control unit 40 divides the partial images 50 and 51 by the plurality of vertical lines 56 and the plurality of horizontal lines 57, and recognizes, as first to n-th corresponding regions, the grids at the same position in the partial images 50 and 51, from the upper left grid to the lower right grid of the partial images 50 and 51. The partial images 50 and 51 are divided into n region images by the n corresponding regions.

The control unit 40 sets i to 1 as an initial value (step S104).

The control unit 40 determines whether or not at least one region image including a specific feature is included in a set of the region images including the region image of the partial image 50 and the region image of the partial image 51 which are represented in the i-th corresponding regions (step S105). The specific feature detected in step S102 is included in the region image hatched in gray in FIG. 9.

In a case where a region image including a specific feature is included in the set of the region images represented in the i-th corresponding regions (YES in step S105), the control unit 40 determines a parameter indicating a degree of application of each region image to the combination image (step S106). In the following, this processing is referred to as parameter determination processing (1). Details of the parameter determination processing (1) will be described later. In a case where a region image including a specific feature is not included in the set of the region images represented in the i-th corresponding regions (NO in step S105), the control unit 40 proceeds to processing of step S107.

The control unit 40 determines whether or not i=n is satisfied (step S107). That is, the control unit 40 determines whether or not determination in step S105 is completed for all the corresponding regions. In a case where i=n is not satisfied (NO in step S107), the control unit 40 increments a value of i by 1 (step S108), and returns to processing of step S105. In a case where i=n is satisfied (YES in step S107), the control unit 40 determines a parameter for the corresponding regions for which the parameter is not determined by referring to the parameters of other corresponding regions for which the parameter is already determined (step S109). In the following, this processing is referred to as parameter determination processing (2). Details of the parameter determination processing (2) will be described later.

The control unit 40 generates a combination region image by combining the region images for each set of the corresponding regions according to the parameter (step S110). Here, first, the control unit 40 superimposes the region images, based on the degree of application which is set as a parameter, for each set of the n corresponding regions. Therefore, n combination region images in which the parameter is reflected are generated. The control unit 40 generates desired combination images (partial images) by arranging and combining the n combination region images according to the positions of the corresponding regions. By further arranging and combining the combination images according to the imaging positions by the imaging unit 38 on the X-Y plane, the entire combination image is generated.

The parameter determination processing (1) and the parameter determination processing (2) will be specifically described. First, the parameter determination processing (1) in a case where a region image including a specific feature is included in the set of the region images represented in the corresponding regions will be described. In the parameter determination processing (1), there is a case where a specific feature is included in a plurality of region images included in the set of the region images represented in the corresponding regions.

Figure 10:
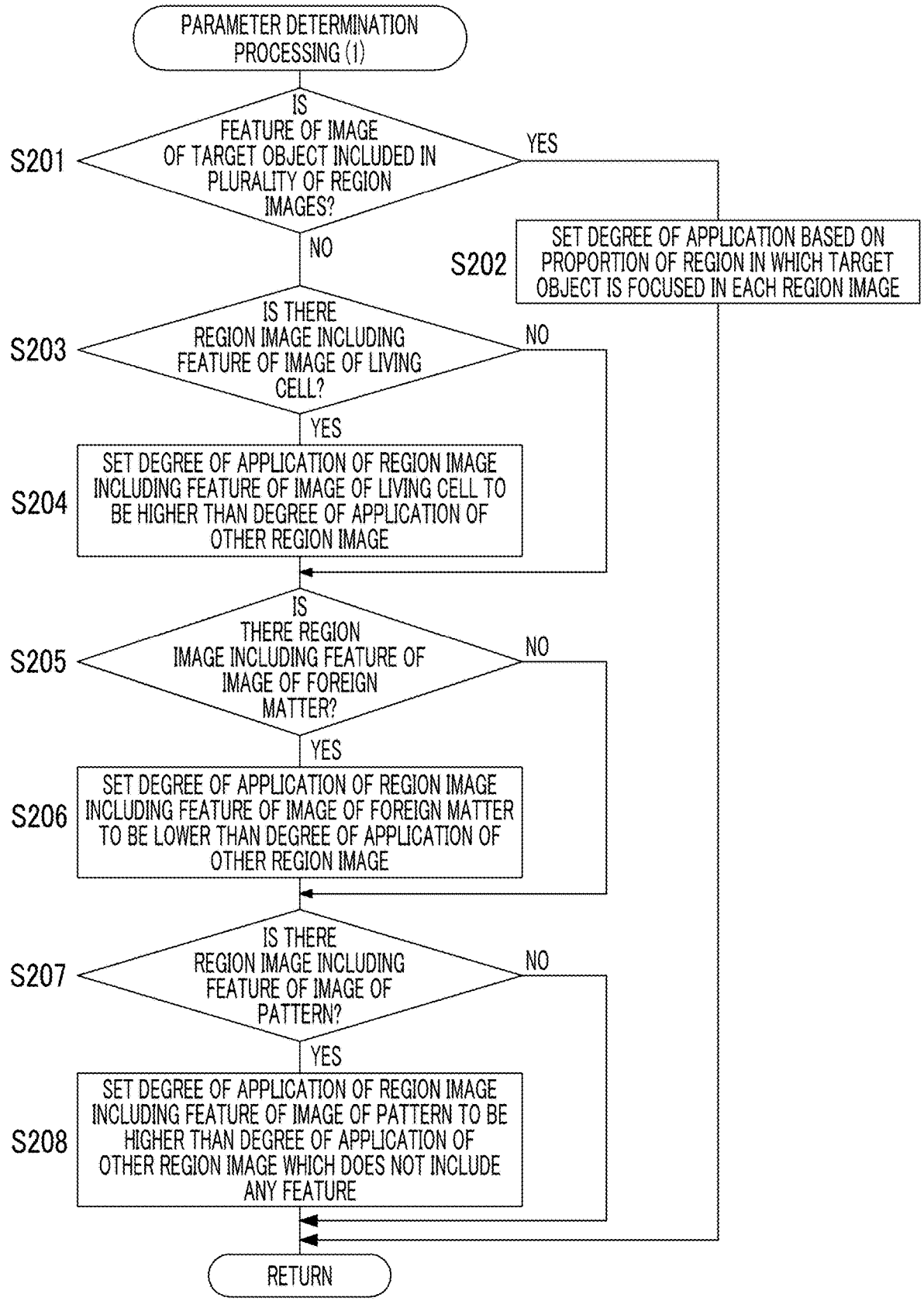
FIG. 10 is a flowchart illustrating a flow of parameter determination processing (1).
Figure 11:
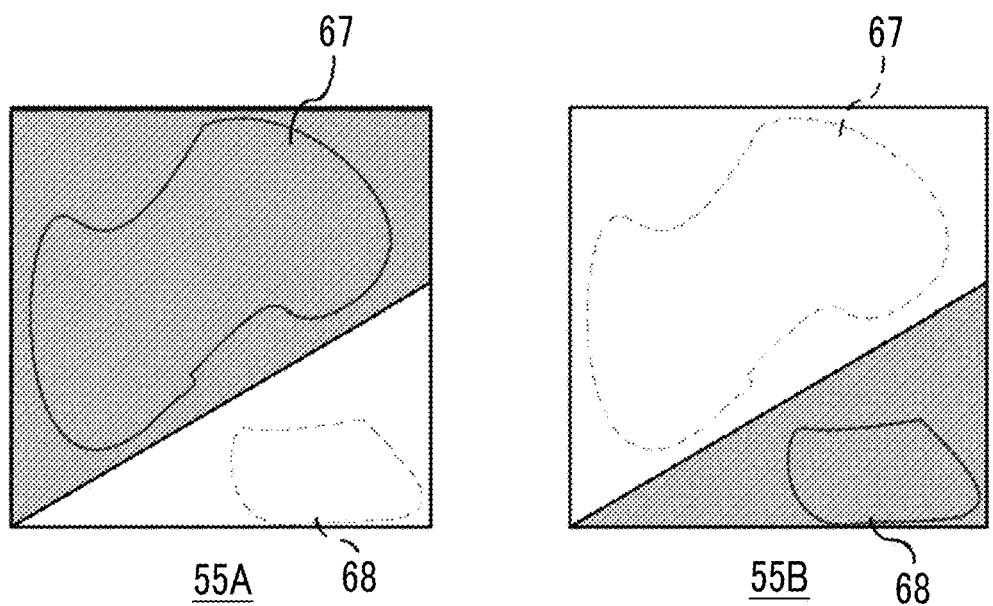
FIG. 11 is a diagram illustrating an example of a plurality of region images in different focus states.

FIG. 10 is a flowchart illustrating a flow of the parameter determination processing (1). FIG. 11 is a diagram illustrating an example of a plurality of region images in different focus states.

The control unit 40 determines whether or not a feature of the image of the target object is included in the plurality of region images included in the set of the region images (step S201). In a case where the plurality of region images do not include a feature of the image of the target object (NO in step S201), the control unit 40 proceeds to processing of step S203.

In a case where the plurality of region images include a feature of the image of the target object (YES in step S201), the control unit 40 determines a degree of application of each region image to the combination image based on a proportion of a region in which the target object is focused in each region image (step S202).

For example, as illustrated in FIG. 11, it is assumed that the corresponding region image 55A and the corresponding region image 55B include images of a living cell 67 and a living cell 68 as target objects. Here, in the region image 55A, the living cell 67 is focused, and the living cell 68 is not focused. On the other hand, in the region image 55B, the living cell 68 is focused, and the living cell 67 is not focused. The control unit 40 obtains a proportion of an area occupied by the living cell 67 which is focused in the region image 55A. The control unit 40 calculates, for example, 60% as a proportion of an area in focus. Further, the control unit 40 obtains a proportion of an area occupied by the living cell 68 which is focused in the region image 55B. The control unit 40 calculates, for example, 40% as a proportion of an area in focus. From the calculation results, the control unit 40 determines a parameter by setting a ratio between a degree of application of the region image 55A to the combination image and a degree of application of the region image 55B to the combination image to 60:40. In this way, the control unit 40 can determine a degree of application of each region image 55 by using a proportion of an area occupied by the target object which is focused.

In FIG. 11, a proportion of an area occupied by the target object is 60% in the region image 55A, a proportion of an area occupied by the target object is 40% in the region image 55B, and a total of the proportions is 100%. On the other hand, even in a case where the total of the proportions of the areas occupied by the target objects in each region image 55 is not 100%, there is no particular problem. For example, even in a case where the proportion of the area occupied by the target object is 70% in the region image 55A and the proportion of the area occupied by the target object is 50% in the region image 55B, a ratio between a degree of application of the region image 55A and a degree of application of the region image 55B is 70:50 (7:5).

In FIG. 11, a case where the target object is a living cell has been described. On the other hand, even in a case where the pattern of the bottom surface of the accommodation portion 22, which is another target object, is included in the region image, as in the case where the target object is a living cell, in each region image, a degree of application of each region image can be determined by using a proportion of an area occupied by the pattern of the bottom surface of the accommodation portion 22, which is the target object.

Returning to the description of FIG. 10, the control unit 40 determines whether or not there is a region image including a feature of an image of a living cell as a specific feature in the set of the region images (step S203). In a case where there is no region image including a feature of an image of a living cell (NO in step S203), the control unit 40 proceeds to processing of step S205. In a case where there is a region image including a feature of an image of a living cell (YES in step S203), the control unit 40 sets a degree of application of the region image including an image of a living cell to be higher than a degree of application of the other region image included in the set (step S204). For example, the control unit 40 determines a parameter by setting a ratio between a degree of application of the region image including a feature of an image of a living cell and a degree of application of the other region image included in the set to 100:0. The ratio between degrees of application is not limited to 100:0, and any ratio may be set as long as the degree of application of the region image including an image of a living cell is higher.

Subsequently, the control unit 40 determines whether or not there is a region image including a feature of an image of a foreign matter as a specific feature in the set of the region images (step S205). In a case where there is no region image including a feature of an image of a foreign matter (NO in step S205), the control unit 40 proceeds to processing of step S207. In a case where there is a region image including a feature of an image of a foreign matter (YES in step S205), the control unit 40 sets a degree of application of the region image including a feature of an image of a foreign matter to be lower than a degree of application of the other region image included in the set (step S206). For example, the control unit 40 determines a parameter by setting a ratio between a degree of application of the region image including a feature of an image of a foreign matter and a degree of application of the other region image included in the set to 0:100. The ratio between degrees of application is not limited to 0:100, and any ratio may be set as long as the degree of application of the region image including a feature of an image of a foreign matter is lower. In addition, in a case where one region image includes both of a feature of an image of a living cell and a feature of an image of a foreign matter as specific features, the feature of the image of the living cell is prioritized, and a degree of application of the region image may not be set to be lower even though a feature of an image of a foreign matter is included.

Subsequently, the control unit 40 determines whether or not there is a region image, which includes a feature of an image of a pattern on the bottom surface of the accommodation portion 22 as a specific feature, in the set of the region images (step S207). In a case where there is no region image including a feature of an image of a pattern (NO in step S207), the control unit 40 proceeds to processing of step S107 of FIG. 8. In a case where there is a region image including a feature of an image of a pattern (YES in step S207), the control unit 40 sets a degree of application of the region image including a feature of an image of a pattern to be higher than a degree of application of the other region image included in the set (step S208). For example, the control unit 40 determines a parameter by setting a ratio between a degree of application of the region image including a feature of an image of a pattern and a degree of application of the other region image included in the set to 100:0, and proceeds to processing of step S107 of FIG. 8. The ratio between degrees of application is not limited to 100:0, and any ratio may be set as long as the degree of application of the region image including a feature of an image of a pattern is higher. Further, even though there is a region image including a feature of an image of a pattern as a specific feature, in a case where the other region image includes another specific feature, a degree of application of the region image including the pattern may not be set to be higher. As described above, living cells have a property of easily sticking to irregularities along a pattern. Thus, in a case where the bottom surface of the accommodation portion 22 is focused and a feature of an image of a pattern is detected, living cells attached to the bottom surface of the accommodation portion 22 may also be focused. Therefore, it is important to increase a degree of application of the region image including a feature of the image of the pattern.

As described above, in a case where a specific feature is included in the region image which is included in the set of the region images represented in the corresponding regions, a parameter is determined according to a type of the specific feature.

Next, the parameter determination processing (2) in a case where a region image including a specific feature is not included in the set of the region images represented in the corresponding regions will be described.

Figure 12:
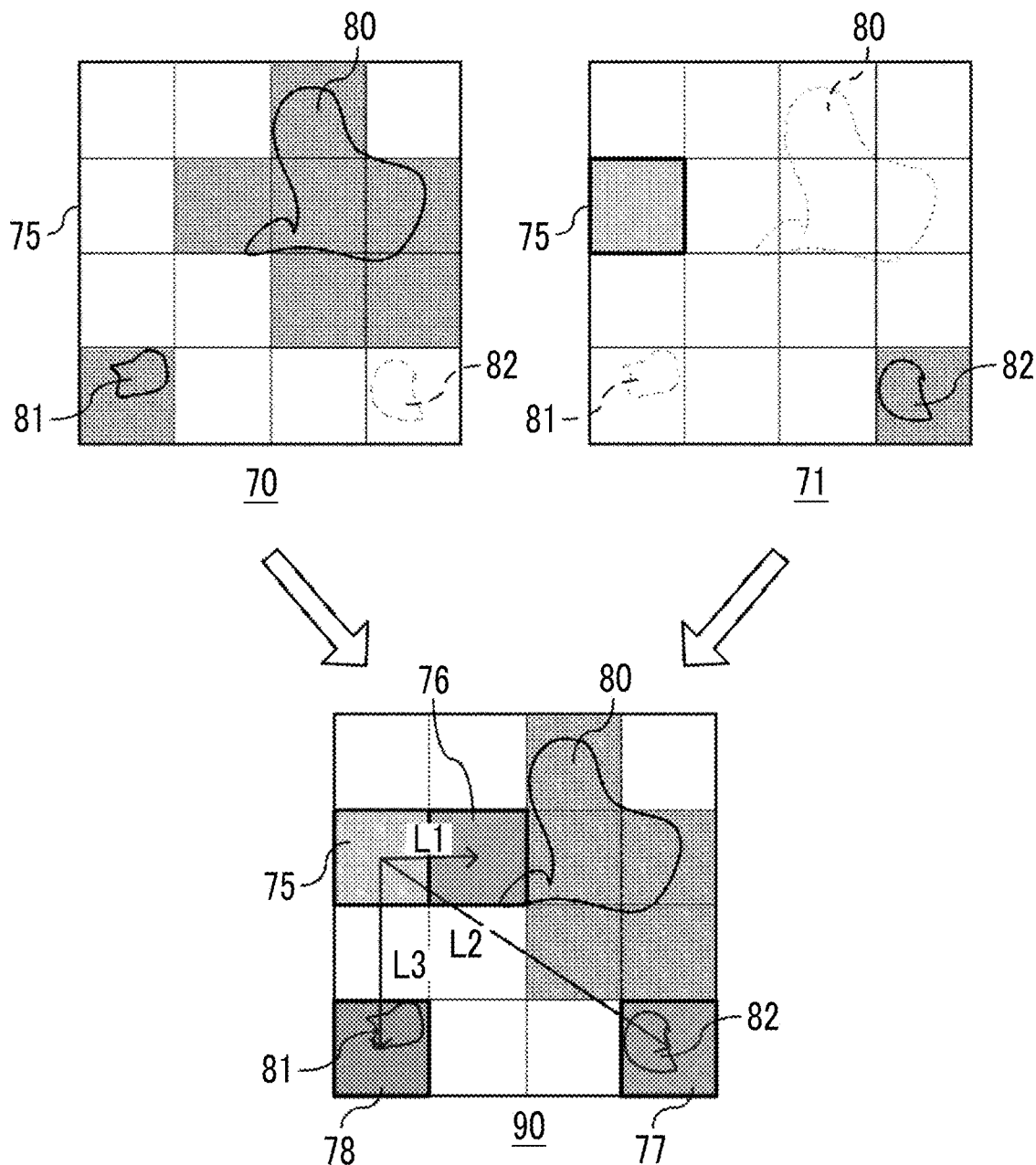
FIG. 12 is a diagram for explaining determination of a parameter in a case where a specific feature is not included in a set of region images represented in corresponding regions.
Figure 13:
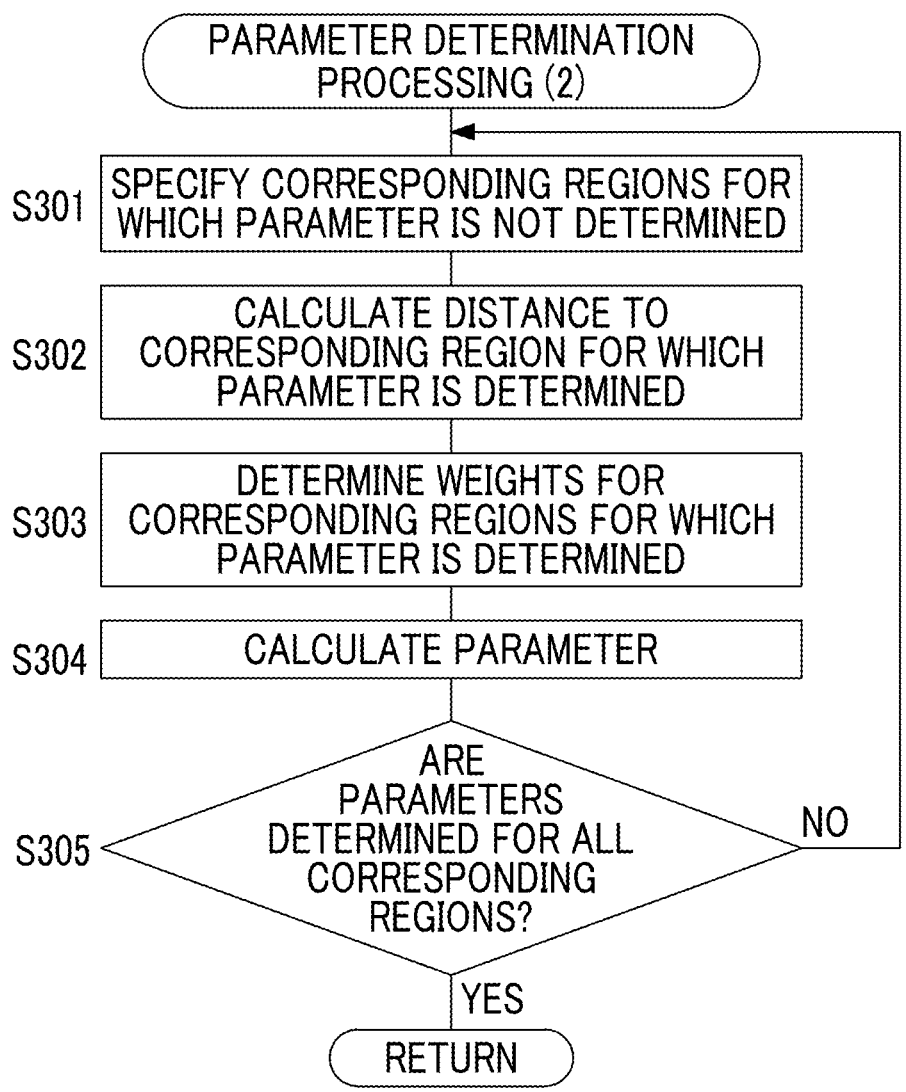
FIG. 13 is a flowchart illustrating a flow of parameter determination processing (2).

FIG. 12 is a diagram for explaining determination of a parameter in a case where a specific feature is not included in the set of the region images represented in the corresponding regions. FIG. 13 is a flowchart illustrating a flow of the parameter determination processing (2).

In FIG. 12, two upper partial images 70 and 71 are partial images imaged at different imaging positions in the Z direction, and a lower partial image 90 is a partial image obtained by superimposing and combining the partial image 70 and the partial image 71. In the partial image 70, living cells 80 and 81 are detected, and in the partial image 71, a feature of an image of a living cell 82 is detected as a specific feature. The region images including features of images of the living cells 80 to 82 are illustrated by hatching in FIG. 12. For the corresponding regions including the hatched region images, a parameter is determined as illustrated in FIG. 10, and the parameter is reflected in the partial image 90. For the remaining corresponding regions, a parameter is determined as illustrated in FIG. 13.

In processing illustrated in FIG. 13, in consideration of a parameter, which is set for a set of region images including a region image in which a specific feature is detected by the control unit 40, a parameter for a set of region images including only a region image in which a specific feature is not detected is determined. For example, for the corresponding regions in which the specific feature is not detected in any region image, the control unit 40 determines a parameter based on a parameter of other corresponding regions in which a certain specific feature is detected and a distance to other corresponding regions. The reason is as follows. For example, living cells are often collected on the bottom surface of the accommodation portion 22, and dead cells are often collected (floated) on the liquid surface of the culture solution. As described above, the target object and the non-target object detected as a specific feature are often collected in the same type. For this reason, as a region image is closer to the region image including a detected specific feature, the region image is likely to have the same specific feature even in a case where the specific feature is not detected. Therefore, by applying, to the parameter, a weight which is inversely proportional to the distance, the target object is likely to be represented in the combination region image and the non-target object is unlikely to be represented in the combination region image.

The control unit 40 specifies the corresponding regions for which the parameter is not determined (step S301). In the following, a case where the corresponding region 75 illustrated in FIG. 12 is specified in step S301 will be described.

The control unit 40 calculates a distance from the corresponding region 75 to the corresponding region for which the parameter is determined (step S302). Here, the corresponding region for which the parameter is determined indicates the corresponding region for which the parameter is determined by the parameter determination processing (1) illustrated in FIG. 10. In a case of the partial image 90 of FIG. 12 obtained by superimposing the two partial images, the hatched corresponding region is the corresponding region for which the parameter is determined. In a case where the continuous corresponding regions for which the parameter is determined based on the same specific feature are regarded as one group, only one corresponding region closest to the corresponding region 75 in one group can be picked up. In the group of the corresponding regions in which the living cell 80 is detected, the corresponding region 76 is closest to the corresponding region 75. Similarly, in the group of the corresponding regions in which the living cell 81 and the living cell 82 are respectively detected, the corresponding regions 77 and 78 are closest to the corresponding region 75. In step S302, distances L1, L2, and L3 from the corresponding region 75 to the corresponding regions 76 to 78 are calculated. The distances L1, L2, and L3 are obtained, for example, as distances from the center of the corresponding region 75 to the centers of the corresponding regions 76 to 78.

The control unit 40 determines weights for the corresponding regions 76 to 78 for which the parameter is determined, using the calculated distances L1, L2, and L3 (step S303). The weight is determined to be a value inversely proportional to the distance. That is, as the region is closer to the corresponding region 75, the weight is determined to be higher. For example, for the corresponding region 76 separated from the corresponding region 75 by the distance L1, a weight $W_{76}$ is determined by the following Equation (1).

[Equation 1]

$$W_{76} = \frac{\frac{1}{L1}}{\frac{1}{L1} + \frac{1}{L2} + \frac{1}{L3}} = \frac{L2L3}{L2L3 + L1L3 + L1L2} \quad \text{Equation (1)}$$

Similarly, a weight $W_{77}$ for the corresponding region 77 separated from the corresponding region 75 by the distance L2 and a weight $W_{78}$ for the corresponding region 78 separated from the corresponding region 75 by the distance L3 are also determined by substituting the numerators of Equation (1) from 1/L1 to 1/L2 and 1/L3. It is noted that $W_{76}+W_{77}+W_{78}=1$.

The control unit 40 calculates a parameter of the corresponding region 75 using the weights (step S304). In a case where the calculated parameter is represented by $P_{75}$ and the parameters of the corresponding regions 76 to 78 are represented by $P_{76}$ to $P_{78}$, the following Equation (2) is obtained.

$$P_{75}=W_{76} \times P_{76}+W_{77} \times P_{77}+W_{78} \times P_{78} \quad \text{Equation (2)}.$$

The calculation will be described in more detail by exemplifying specific numerical values. In the following example, simply, it is assumed that the weights $W_{76}$, $W_{77}$, and $W_{78}$ are respectively ½, ¼, and ¼. Further, it is assumed that the determined parameters $P_{76}$, $P_{77}$, and $P_{78}$ are respectively (100,0), (0,100), and (100,0). Here, (100,0) indicates that a ratio between degrees of application of the region images of the partial image 70 and the region images of the partial image 71 in a case of forming the partial image 90 is 100:0.

The specific numerical values are substituted to Equation (2), and thus $P_{75}=\frac{1}{2}\times(100,0)+\frac{1}{4}\times(0,100)+\frac{1}{4}\times(100,0)=(50,0)+(0,25)+(25,0)=(75,25)$. That is, in the case of forming the partial image 90 with reference to the corresponding region 75, the degree of application of the partial image 70 is 75%, and the degree of application of the partial image 71 is 25%.

The control unit 40 determines whether or not the parameters are determined for all the corresponding regions (step S305). In a case where the parameters are not determined for all the corresponding regions (NO in step S305), the control unit 40 returns to processing of step S301. In a case where the parameters are determined for all the corresponding regions (YES in step S305), the control unit 40 returns to processing of step S110 in FIG. 8.

In the above description, one corresponding region 76 (77, 78) of one group of continuous corresponding regions in which the specific feature is detected is picked up, and the picked-up corresponding region is used for determination of the parameters of the corresponding regions in which the specific feature is not included. On the other hand, in one group of the corresponding regions, all the corresponding regions in which the specific feature is detected may be used for determination of the parameters of the corresponding regions in which the specific feature is not included.

As described above, according to the observation device of the present embodiment, for each set of region images represented in corresponding regions of a plurality of images imaged at different imaging positions in the Z direction, a parameter indicating a degree of application to a combination region image is determined, and a combination region image is combined based on the parameter. In a case where an image of a target object is included in a plurality of region images in the set of the region images, the control unit 40 determines a parameter indicating a degree of application based on a proportion of an area of a region in which the target object is focused in each region image. Thus, in a case where a plurality of target objects are focused with different focuses in the Z direction, a degree of application of a region image having a larger focus area is increased, and a region image having a small focus area is also applied to the combination image. Therefore, the image of the target object represented in any region image is applied to the combination image. As a result, in a case where a user refers to the combination image, all target objects existing at different positions in the Z direction can be recognized.

Further, even in a case where the set of the region images includes only a region image in which a specific feature is not detected by the control unit 40, the specific feature can be applied to the combination region image based on a degree of application of a parameter of a region image close to the region image. By arranging and combining the combination region images according to positions of the corresponding regions, a combination image is generated. As described above, the combination image is generated, and thus, in a case where a user visually confirms the combination image, the specific feature can be confirmed. Further, the entire combination image is generated by arranging and combining the combination images according to the imaging positions, and thus, in a case where a user visually confirms the entire combination image, the specific feature may be confirmed.

In addition, as illustrated in FIG. 10, the observation device determines a parameter by setting a degree of application of the region image including a feature of an image of a living cell to the combination region image to be higher than a degree of application of the region image that does not include a feature of an image of a living cell to the combination region image. Therefore, the image of the living cell is likely to be represented in the combination region image, and thus the image of the living cell is likely to be represented in the combination image.

In addition, the observation device determines a parameter by setting a degree of application of the region image including a feature of an image of a foreign matter to the combination region image to be lower than a degree of application of the region image that does not include a feature of an image of a foreign matter to the combination region image. Therefore, the image of the foreign matter is unlikely to be represented in the combination region image, and thus the image of the foreign matter is unlikely to be represented in the combination image.

In addition, the observation device determines a parameter by setting a degree of application of the region image including a feature of an image of a pattern to the combination region image to be higher than a degree of application of the region image that does not include both of a feature of an image of a living cell and a feature of an image of a foreign matter to the combination region image. Therefore, the image of the pattern is likely to be represented in the combination region image.

In addition, the observation device determines whether or not a specific feature is detected in any region image for each corresponding region, and, for the corresponding regions in which the specific feature is not detected in any region image, determines a parameter based on a parameter of other corresponding regions in which a certain specific feature is detected and a distance to other corresponding regions. Accordingly, in a case where the set of the region images including only a region image in which a specific feature is not detected is combined, the target object (living cell) is likely to be represented in the combination region image, and the non-target object is unlikely to be represented in the combination region image.

The present disclosure is not limited to the embodiment. Various modifications may be made.

For example, in the processing illustrated in FIG. 13, for the corresponding regions in which the specific feature is not detected in any region image, a parameter is determined based on a parameter of other corresponding regions in which a certain specific feature is detected and a distance to other corresponding regions. On the other hand, in a case where a parameter is determined for the corresponding regions in which a specific feature is not detected in any region image, the parameter of other corresponding regions may not be considered. For example, for the corresponding regions in which a specific feature is not detected in any region image, a parameter may be determined according to a predetermined degree of application. Here, the predetermined degree of application may be the same, for example, in the region images represented in the corresponding regions. Specifically, for example, in a case of two region images represented in the corresponding regions, the degree of application may be 50:50.

Further, in the processing illustrated in FIG. 13, for the corresponding regions in which a specific feature is not detected in any region image, a parameter is determined. In addition to the parameter determination or instead of the parameter determination, the observation device may further include a warning unit that outputs a warning to the user. The warning unit can be realized as one function of the control unit 40. For example, the warning unit causes the display unit 48 to display a warning message for notifying a user that there are corresponding regions in which a specific feature is not detected in any region image. Thereby, a user is warned of whether or not a specific feature is ignored in the corresponding regions in which a specific feature is not detected in any region image. In some cases, a user can determine whether or not a specific feature is ignored by confirming the partial images before combination.

Further, in the embodiment, an example in which the microscope device 30 performs imaging of partial images of the observation target and the culture container 20 has been described. On the other hand, the microscope device 30 may have a field of view for imaging of the entire of the observation target and the culture container 20, such as in a case where imaging is performed at a lower magnification than a magnification in imaging of the partial images, and may image the entire image instead of the partial images. Even in this case, the entire image may be divided into region images, and a parameter may be given to each region image. Thereby, a combination image may be obtained. In this case, the obtained combination image is not the partial image but the entire image.

Further, in the embodiment, various processors other than the CPU may execute the observation processing executed by reading software (program) by the CPU. In this case, examples of the processor include a programmable logic device (PLD) of which a circuit configuration may be changed after manufacturing, such as a field-programmable gate array (FPGA), and a dedicated electric circuit which is a processor having a circuit configuration specially designed for executing specific processing, such as an application specific integrated circuit (ASIC). In addition, the observation processing may be executed by one of these various processors, or may be executed by a combination of two or more processors having the same type or different types (for example, a plurality of FPGAs, a combination of a CPU and an FPGA, or the like). Further, hardware structures of these various processors include, more specifically, electric circuits in which circuit elements such as semiconductor elements are combined.

Further, in the embodiment, an example in which the microscope device 30 includes the two imaging units 38a and 38b has been described. On the other hand, the present disclosure is not limited thereto, and one imaging unit may perform imaging of an observation target at a plurality of different imaging positions in the Z direction.

Further, in the embodiment, an example in which an observation processing program is stored (installed) in the storage unit 43 in advance has been described. On the other hand, the present disclosure is not limited thereto. The program may be provided by being recorded in a recording medium such as a compact disk read only memory (CD-ROM), a digital versatile disk read only memory (DVD-ROM), and a Universal Serial Bus (USB) memory. Further, the program may be downloaded from an external device via a network.

EXPLANATION OF REFERENCES

10: placing stand
11: opening

12: moving unit
20: culture container
21: plate
22: accommodation portion
30: microscope device
31: light source
32: slit
33: condenser lens
34: objective lens
35: focus adjustment mechanism
36: image-forming lens
37: half mirror
38, 38a, 38b: imaging unit
39: measurement unit
39a: first displacement sensor
39b: second displacement sensor
40: control unit
41: microscope device control unit
42: scanning control unit
43: storage unit
44: detection unit
45: determination unit
46: generation unit
47: input unit
48: display unit
50, 51, 70, 71, 90: image
55, 75 to 78: corresponding region
56: vertical line
57: horizontal line
60 to 63, 80 to 82: living cell
64: dead cell
65: detritus
66: pattern
C: image-forming optical system
E: scanning end point
L1, L2, L3: distance
L: illumination light
M: scanning path
R: field of view

What is claimed is:

1. An image generation device comprising:
a processor configured to
  perform processing of detecting a specific feature from a plurality of focus images which include an observation target and are in different focus states;
  determine a parameter indicating a degree of application of a region image to a combination region image in a case where the combination region image is generated from the region image, for each set of the region images in a plurality of corresponding regions respectively corresponding to the plurality of focus images, based on the specific feature; and
  generate the combination region image by combining the region images for each of the plurality of corresponding regions based on the parameter,
wherein the processor determines a parameter for a set of the region images that do not include the detected specific features in any region image, based on a parameter determined for a set of the region images that include the detected specific feature in any region image.

2. The image generation device according to claim 1, wherein the processor determines the parameter for the set of the region images that do not include the specific feature in any region image, based on a distance from the corresponding regions of the set of the region images that include the specific feature in any region image to the corresponding regions of the set of the region images that do not include the specific feature in any region image.

3. The image generation device according to claim 1, wherein the processor generates a combination image by arranging and combining the combination region images according to positions of the corresponding regions.

4. The image generation device according to claim 2, wherein the processor generates a combination image by arranging and combining the combination region images according to positions of the corresponding regions.

5. The image generation device according to claim 1, wherein the processor generates a combination image by arranging and combining the combination region images according to positions of the corresponding regions.

6. The image generation device according to claim 1, wherein the specific feature is at least one of a feature of an image of a target object included in the observation target or a feature of an image of a non-target object included in the observation target.

7. The image generation device according to claim 2, wherein the specific feature is at least one of a feature of an image of a target object included in the observation target or a feature of an image of a non-target object included in the observation target.

8. The image generation device according to claim 6, wherein, in a case where the feature of the image of the target object is included in the region image, the processor determines the parameter by setting a degree of application of the region image including the feature of the image of the target object to the combination region image to be higher than a degree of application of the region image that does not include the feature of the image of the target object to the combination region image, and in a case where the feature of the image of the non-target object is included in the region image, the processor determines the parameter by setting a degree of application of the region image including the feature of the image of the non-target object to the combination region image to be lower than a degree of application of the region image that does not include the feature of the image of the non-target object to the combination region image.

9. The image generation device according to claim 6, wherein, in a case where a plurality of region images including the feature of the target object exist in a set of the region images in one corresponding region, the processor determines a parameter for each region image based on a proportion of an area occupied by the feature of the target object in each region image.

10. The image generation device according to claim 6, wherein the target object is a living cell, and the non-target object is a foreign matter other than the living cell that is included in the observation target.

11. The image generation device according to claim 10, wherein the processor determines the parameter by setting a degree of application of the region image including a feature of an image of the living cell to the combination region image to be higher than a degree of application of the region image that does not include the feature of the image of the living cell to the combination region image.

12. The image generation device according to claim 10, wherein the processor determines the parameter by setting a degree of application of the region image including a feature of an image of the foreign matter to the combination region image to be lower than a degree of application of the region image that does not include the feature of the image of the foreign matter to the combination region image.

13. The image generation device according to claim 10, wherein the target object includes, in addition to the living cell, a pattern represented on a bottom surface of an accommodation portion, and the processor determines the parameter by setting a degree of application of the region image including a feature of an image of the pattern to the combination region image to be higher than a degree of application of the region image that does not include both of the feature of the image of the living cell and the feature of the image of the foreign matter to the combination region image.

14. The image generation device according to claim 1, the processor further configured to:

output a warning for the corresponding region in which the specific feature is not detected in any region image.

15. An image generation method comprising:

detecting a specific feature from a plurality of focus images which include an observation target and are in different focus states;

determining a parameter indicating a degree of application of a region image to a combination region image in a case where the combination region image is generated from the region image, for each set of the region images in a plurality of corresponding regions respectively corresponding to the plurality of focus images, based on the specific feature detected by the detection step; and generating the combination region image by combining the region images for each of the plurality of corresponding regions based on the parameter determined by the determination step, wherein the determination step, the parameter is determined for a set of the region images that do not include the detected specific feature in any region image, based on a parameter determined for a set of the region images that include the detected specific feature in any region image.

16. A non-transitory computer readable recording medium storing an image generation program causing a computer to execute:

detecting a specific feature from a plurality of focus images which include an observation target and are in different focus states;

determining a parameter indicating a degree of application of a region image to a combination region image in a case where the combination region image is generated from the region image, for each set of the region images in a plurality of corresponding regions respectively corresponding to the plurality of focus images, based on the specific feature detected by the detection step; and generating the combination region image by combining the region images for each of the plurality of corresponding regions based on the parameter determined by the determination step, wherein the determination step, the parameter is determined for a set of the region images that do not include the detected specific feature in any region image, based on a parameter determined for a set of the region images that include the detected specific feature in any region image.

* * * * *